United States Patent [19]

Torelli et al.

[11] 4,444,767
[45] Apr. 24, 1984

[54] DERIVATIVES OF 3-AMINO-PREGN-5-ENE

[75] Inventors: Vesperto Torelli, Maisons-Alfort; Josette Benzoni, Livry Gargan; Roger Deraedt, Pavillons sous Bois, all of France

[73] Assignee: Roussel Uclaf, Paris, France

[21] Appl. No.: 436,524

[22] Filed: Oct. 25, 1982

[30] Foreign Application Priority Data

Oct. 27, 1981 [FR] France ............................ 81 20135

[51] Int. Cl.$^3$ ............................................. A61K 31/56
[52] U.S. Cl. .................................. 424/238; 260/397.3; 260/397.5
[58] Field of Search .................. 260/397.3, 397.5; 424/238

[56] References Cited

PUBLICATIONS

Chem. Abstracts, vol. 95, (1981) Par. 151001p Article by Frappier et al., J. Org. Chem. 1981, No. 46 (21) pp. 4314–4315.

*Primary Examiner*—Elbert L. Roberts
*Attorney, Agent, or Firm*—Bierman, Bierman, Peroff & Muserlian

[57] ABSTRACT

A compound selected from the group consisting of: 3-amino-$\Delta^5$-pregnenes of the formula I:

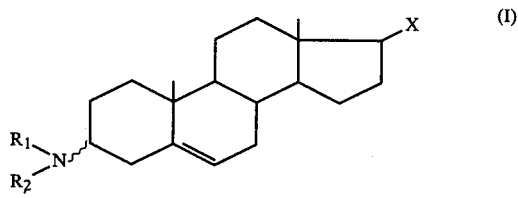

wherein X is selected from the group of

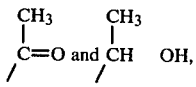

the wavy lines indicate that the group may be in the α-or β-position, $R_1$ is selected from the group consisting of hydrogen and hydroxyalkyl or 2 to 5 carbon atoms, $R_2$ is selected from the group consisting of hydrogen, hydroxyalkyl of 2 to 5 carbon atoms, acyl of an aliphatic carboxylic acid of 3 to 8 carbon atoms, alkoxycarbonyl of 2 to 8 carbon atoms, acyl of an α-amino-carboxylic acid or from a peptide of 2 to 3 amino acids of which amines may be either unsubstituted or mono-or disubstituted with alkyl of 1 to 5 carbon atoms with the proviso that $R_1$ and $R_2$ are not both hydrogen and that if the 3-amino group is in the β-position, (i) when X is

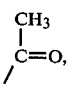

$R_1$ and $R_2$ are not both hydroxyethyl or (ii) when X is

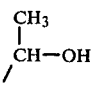

and $R_1$ is hydrogen, $R_2$ is not ethoxycarbonyl, the compound of the formula I wherein X is

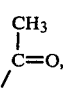

$R_1$ is hydrogen and $R_2$ is methyl, the 3-amino group is in the α-position and their non-toxic, pharmaceutically acceptable acid addition salts which are useful as stimulants of the mammalian immune system.

18 Claims, No Drawings

DERIVATIVES OF 3-AMINO-PREGN-5-ENE

BACKGROUND OF THE INVENTION

The commonly assigned U.S. application Ser. No. 177,845 filed Aug. 14, 1980, now abandoned, and Ser. No. 292,791 filed Aug. 14, 1981 related to steroids. Belgian patent 701,968 of 1968 describes alkaloids extracted from the leaves of plants, some of which are 3α-amino pregn-5-ene which are described as having antibacterial, antifungal, and antiviral properties. The antibacterial character of some compounds was demonstrated in vitro experiments.

OBJECTS OF THE INVENTION

It is an object of the invention to provide novel derivatives of 3-amino-pregn-5-ene of formula I and their nontoxic, pharmaceutically acceptable acid addition salts.

It is a further object of the invention to provide a method for the preparation of the said 3-amino-pregn-5-enes and their nontoxic, pharmaceutically acceptable acid addition salts.

It is another object of the invention provided novel compositions containing 3-amino-pregn-5-enes of formula I and their nontoxic, pharmaceutically acceptable acid addition salts which act as stimulants of the mammalian immune system and a method of stimulating immune systems of warm blooded animals.

These and other objects of the invention will become more apparent as the description thereof proceeds.

DESCRIPTION OF THE INVENTION

The novel compounds of the invention are selected from the group consisting of:
3-amino-pregn-5-enes of the formula:

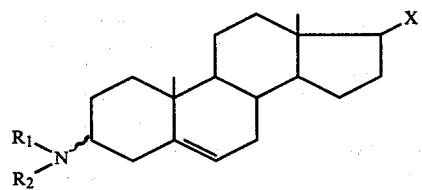

in which X is selected from the group consisting of

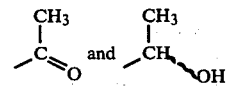

the wavy line indicates the radical to which it is attached may be in the α or the β position, $R_1$ is hydrogen or a hydroxy alkyl radical containing 2 to 5 carbon atoms, $R_2$ is selected from the group consisting of hydrogen, hydroxy alkyl radical containing 2 to 5 carbon atoms, acyl of an aliphatic carboxylic acid containing 3 to 8 carbon atoms, alkoxy carbonyl containing 2 to 8 carbon atoms, acyl of an α amino acid or from a peptide having 2 or 3 amino acid units of which the amine is unsubstituted, or monosubstituted or disubstituted by an alkyl radical of 1 to 5 carbon atoms with the proviso that $R_1$ and $R_2$ are not both hydrogen at the same time and that if the amino group is in the β position
(i) when X is

$R_1$ and $R_2$ may not be both hydroxy ethyl radicals
(ii) when X is

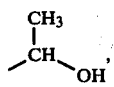

and $R_1$ is hydrogen, then $R_2$ may not be ethoxy carbonyl the compound of the formula I wherein X is

$R_1$ is hydrogen, $R_2$ is methyl and the amino group is in the α position
and their non toxic, pharmaceutically acceptable acid addition salts.

In formula I and in those which follow the alkyl radical is one having 1 to 5 carbon atoms such as methyl, ethyl, propyl, isopropyl, butyl, isobutyl or pentyl. The hydroxyalkyl radical is one containing 2 to 5 carbon atoms such as hydroxyethyl or hydroxypropyl. The acyl radical contains 3 to 8 carbon atoms such as propionyl, n-butyryl or isobutyryl. The alkoxycarbonyl contains 2 to 8 carbon atoms such as methoxycarbonyl, ethoxycarbonyl or propoxycarbonyl. The acyl of an α-amino acid may be chosen from the group consisting of Ala, Val, Leu, Ile, Asp, Asn, Glu, Gln, Ser, Thr, Cys, Met, Lys, Arg, Phe, Tyr, Trp, His, Pro, Nva, Nle, Hyp, Orn which may be in the dextro or levo form. Sar or Gly may be used also. When $R_2$ is a radical derived from a peptide comprising 2 or 3 α-amino acid units these are chosen from the aforementioned groups.

When the α-amino acids or the peptides are N-monoalkyl or N-dialkyl substituted, the substituents are preferably methyl, ethyl or propyl.

The conventional symbols for the α-amino acids represent both the dextro and levo forms and the nomenclature used in the present application is that of the IUPAC, the rules for which were published in Biochem. J. (1972) 126, 773–780.

The nontoxic, pharmaceutically acceptable acid addition salts of the compounds of the invention with organic and mineral acids may be hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids, such as methane sulfonic acid and ethane sulfonic acid, aryl sulfonic acids such as benzene sulfonic acid and p-toluene sulfonic acid and aryl carboxylic acids.

Among the preferred products of the invention of formula I and their nontoxic, pharmaceutically acceptable acid addition salts with mineral and organic acids are those wherein the amino group is in the 3-α-position, those wherein $R_1$ is hydrogen and those wherein $R_2$ is a radical derived from an α-amino acid or from a peptide containing 2 or 3 α-amino acid units and among those are especially retained those wherein X is selected from the group consisting of

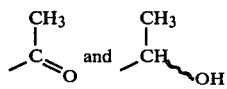

and has a hydroxyl group at the 20α. Very preferred is the 3-α methylamino pregn-5-ene 20-one and other compounds whose preparation is described in the example.

The novel process of the invention comprises reacting an amine of formula II

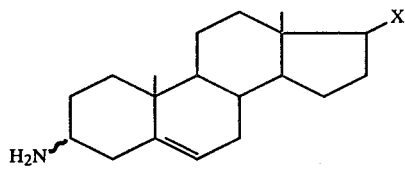 (II)

is which the wavy line and X have the meanings previously indicated, with a halide of the formula Hal—R$_2$' (III)

in which Hal is chlorine, bromine or iodine, R$_2$' is an acyl of an aliphatic carboxylic acid of 3 to 8 carbon atoms or alkoxycarbonyl of 2 to 8 carbon atoms to form a product of formula I in which R$_1$ is hydrogen, R$_2$ is R$_2$' as defined above, and X and the wavy line have the meanings previously indicated which product may be isolated and salified.

The amine of formula II may also be reacted with an acid or acid anhydride of formula III':

A—O—R$_2$'' (III') wherein A is hydrogen or an R$_2$'' radical; R$_2$'' being an acyl aliphatic radical containing 3 to 8 carbon atoms to obtain a product of formula I in which R$_1$ is hydrogen and R$_2$ is R$_2$'' as defined above and X and the wavy line have the same meanings as previously indicated which product may be isolated and salified.

The amine of formula II may also be reacted with an α-amino acid or with a peptide comprised of 2 or 3 α-amino acid units of which the amine function is monosubstituted or disubstituted by an alkyl radical of 1 to 5 carbon atoms or it may be unsubstituted but when unsubstituted it is protected by a group which is easily cleavable by means of acid hydrolysis or by hydrogenolysis, then to proceed in a way to eliminate the protective group thereby obtaining the product of formula I in which R$_1$ is hydrogen, R$_2$ is a radical derived from an α-amino acid or from a peptide containing 2 or 3 α-amino acid units and in which X and the wavy line have the meanings previously indicated. The products may be isolated and salified;

The amine of formula II may also be reacted with a hydroxyalkyl halide of 2 to 5 carbon atoms in which the halogen is chlorine, bromine or iodine to obtain a product of formula I wherein the amine group in the 3 position is monosubstituted or disubstituted by a hydroxyalkyl radical containing 2 to 5 carbon atoms and X and the wavy line have the meanings previously indicated;

In the case where X is

and the amine group is in the 3 α-position, the amine of formula II may be reacted with a methyl halide in order to obtain a compound of formula I wherein X is

R$_1$ is hydrogen, R$_2$ is methyl, the amino group is in the 3 α-position, which may be either isolated and salified or in the case where R$_2$ is hydrogen the said product of formula I may be reacted with a halide of the formula Hal—R$_2$''' (IV)

in which R$_2$''' is a hydroxyalkyl radical having 2 to 5 carbon atoms, an acyl of an aliphatic carboxylic acid of 3 to 8 carbon atoms or an alkoxycarbonyl radical having 2 to 8 carbon atoms and Hal has the previously indicated meanings to obtain the product of formula I in which R$_1$ is hydroxyalkyl containing 2 to 5 carbon atoms, R$_2$ is R$_2$''' which is defined above and X and the wavy line have the meanings previously indicated which may be isolated and salified or else again when R$_2$ is hydrogen the product of formula I may be reacted an α-amino acid or a peptide comprised of 2 to 3 α-amino acid units of which the amine function is monosubstituted or disubstituted by an alkyl radical having 1 to 5 carbon atoms or protected by a group which is easily cleavable, particularly by acid hydrolysis or by hydrogenolysis, then to proceed optionally in a manner to eliminate the protective group to obtain a product of formula I in which R$_1$ is a hydroxy alkyl radical containing 2 to 5 carbon atoms, R$_2$ is a radical derived from an α-amino acid or a peptide comprising 2 or 3 α-amino acid units and X and the wavy line have the meaning previously indicated which may be isolated and salified.

Under the preferred conditions for practicing the invention, the method of preparation described above is one wherein:

(a) The reaction of the amine of formula II with an acid halide of formula III is carried out in the presence of a binding agent for acids.

Particularly suitable are alkalimetal hydroxides, carbonates, or an alkali metal acetate (for example sodium or potassium acetate), an alkaline earth carbonate (for example that of calcium), a tertiary amine such as trialkyl amine or pyridine or an alkali metal alcoholate such as sodium ethylate. The reaction may be carried out in inert solvents or as a suspension in an inert medium such as dioxane, dimethylformamide, benzene, toluene or a halogenated hydrocarbon such as methylene chloride.

(b) The reaction of the amine of formula II with an acid of formula III' is carried out in the presence of an activating agent such as a carbodiimide. Other techniques may be used such as those described in "The Peptides" Vol. 1, Academic Press 1979.

(c) The reaction of an amine of formula II or of a product of formula I in which R$_2$ is a hydrogen atom and R$_1$ is a hydroxyalkyl radical with an α-amino acid or with a peptide comprising 2 or 3 α-amino acid units of which the amino function is monosubstituted or disubstituted or protected by an protective group which is easily cleavable, is carried out in the presence of a condensing agent. The condensing agent has, in this case, for its object activating the acid function of the amino acid.

As the condensing agent, a carbodiimide of the formula: $A_1-N=C=N-B_1$ may be used in which $A_1$ and $B_1$ are alkyl radicals containing 1 to 8 carbon atoms optionally bearing a dialkylamino radical or are cycloalkyl radicals. Examples are dicyclohexylcarbodiimide or 1-ethyl-3-(3-dimethylaminopropyl)-carbodiimide, preferably the latter, as condensing agents. One may likewise employ 2-chloro-N-methylpyridinium halides such as the iodide. One may also employ an alkyl chloroformate such as methyl chloroformate, ethyl chloroformate or isobutyl chloroformate. An alkyl pyrophosphite such as ethyl pyrophosphite may also be used. As the easily cleavable protective group, depending on the case, preferably benzyloxycarbonyl (Z) or tertiary butyloxycarbonyl (BOC) may be used.

To eliminate the easily cleavable protective group, an acid such as hydrochloric acid is used as the cleaving agent; one may employ hydrochloric acid in an alcohol solution or anhydrous hydrochloric acid bubbling in nitromethane. Other acids which may be used are paratoluene sulfonic acid, formic acid or trifluoroacetic acid. Hydrogen may be used in the presence of a palladium catalyst to cleave the protective group Z.

(d) The reaction of an amine of formula II with a methyl halide or a hydroxyalkyl halide takes place in the presence of the same acid binding agents and solvents as were used in the case of the halide of formula III.

The hydroxy function of the hydroxyalkyl is blocked, advantageously, by an easily cleavable protective group, which is removed, particularly by means of acid hydrolysis.

(e) The reaction to produce the product of formula I in which $R_2$ is hydrogen, $R_1$ is hydroxyalkyl containing 2 to 5 carbon atoms and X and the wavy line have the meanings previously indicated is with the halide of formula IV which is carried out, depending on the nature of $R_2'''$ under the conditions previously described for the reaction of the amine of formula II with the halide of formula III.

To prepare the product of formula I having an N-methyl, an amine carbamate of formula II is prepared using for example an alkyl haloformate such as ethyl haloformate, followed by reduction of the carbamate, for example by means of aluminum-lithium hydride.

When X is

it is necessary during the reduction to protect the ketone at the 20 position by means of ethylene glycol, then, after reduction, hydrolysis of the ketal group by means of a mineral acid such as hydrochloric acid.

The derivatives of formula I, with the exception of those in which $R_2$ is an acyl radical or an alkoxycarbonyl show basic characteristics. The nontoxic, pharmaceutically acceptable acid addition salts of the derivatives of formula I are prepared by reacting them in approximately stoichiometric proportions with a mineral acid or an organic acid. The salts can be prepared without isolating the corresponding bases.

The novel compositions of the invention for the treatment of autoimmuno maladies are comprised of at least one compound selected from the group consisting of a compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions.

Example of suitable excipients are talc, arabic gum, lactose, starch, magnesium stearate, cocoa butter, aqueous or non-aqueous vehicles, fatty bodies of vegetable or animal origin, paraffinic derivatives, glycols, diverse wetting agents, emulsifiers or dispersants and preservatives.

The compositions are useful for the treatment of autoimmuno maladies resulting from a deficiency of certain lymphocytes such s maladies of conjunctive tissue which are non-specific of an organ such as rhumatoidal arthritis or systemic erythematous lupus or specific maladies of an organ such as thyroiditis, pemphygus or hemolytic anaemia. The compositions are also useful as adjuvant treatment of anticancer chemotherpy and antibiotherapy.

Among the preferred compositions of the invention are those of formula I in which the amino group is in the 3-α position, these wherein $R_1$ is a hydrogen atom, these wherein $R_2$ is a radical derived from an α-amino acid or from a peptide containing 2 or 3 α-amino acid units and among those are especially retained those wherein X is

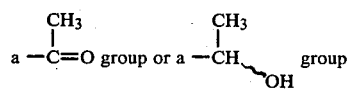

of which the hydroxyl radical is at the 20α-position and their nontoxic pharmaceutically acceptable acid addition salts.

Particularly preferred compositions are those containing 2-amino-N-(20-oxo-pregn-5-ene 3α-yl) acetamide; (2S) 2-amino-N-(20-oxo-pregn-5-ene 3α-yl)-propionamide; 3α-methylamino pregn-5-ene 20-one and their non-toxic, pharmaceutically acceptable acid addition salts.

The novel method of the invention of treating autoimmuno maladies in warm-blooded animals, including humans comprises administering to warm-blooded animals an amount sufficient to treat autoimmuno maladies of at least one compound selected from the group consisting of a compound of of formula I and their non-toxic, pharmaceutically acceptable acid addition salts. The compounds may be administered orally, rectally or parenterally. The usual daily dose is depending on the affection treated, the patient and the method of administration. It can be 0.13 to 13.3 mg/kg per day when administered orally in man as an antibiotherapy adjuvant.

The products of formula II in which X is a

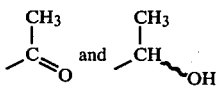

may be prepared by reducing a compound of formula

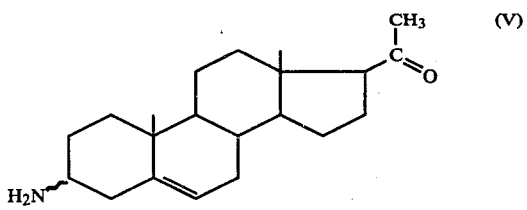

(V)

in which the wavy line has the meaning previously indicated for example, by means of an alkali metal as sodium in a solvent such as a lower aliphatic alcohol such as ethanol to obtain the product of formula

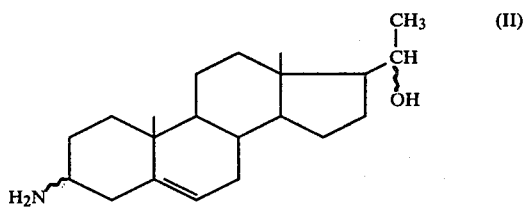

(II)

in which the wavy lines have the same meaning as previously indicated in the form of a mixture of the 20α and 20β isomers which can be separated by preparation of the trifluoroacetyl derivatives of the amine and the alcohol, separating them chromatographically, then hydrolyzing the trifluoroacetyl groups of the separate isomers. An example of such a preparation will be given in the subsequent experimental part.

The amino acids or peptides in which the amine function is monosubstituted or disubstituted may be prepared, when they are not known, by classical methods for alkylating amines.

In the following examples there are described several preferred embodiments to illustrate the invention. However, it should be understood that the invention is not to be limited to the specific embodiments.

EXAMPLE 1

3α-methylamino pregn-5-ene 20-one hydrochloride

Step A: (20-oxo-pregn-5-ene 3α-yl) ethyl carbamate.

6 g of 3α-amino pregn-5-ene-20-one were dissolved in 100 ml of methylene chloride and 22 ml of 1 N NaOH were added at +5° and +10° C. Then in 10 minutes 2 ml of ethyl chloroformate was added and the mixture was stirred for 1 hour.

The reaction mixture was acidified with 15 ml of 2 N HCL, and the decanted, organic phase was washed with water, dried and evaporated to dryness. The residue was dissolved in 70 ml of ethyl ether and the solution refluxed and vacuum filtered. The product was washed with ether and dried to obtain 6.25 g of the desired product melting at 202° C.

Step B: (20, 20-ethylene dioxy pregn-5-ene 3α-yl) ethyl carbamate.

A mixture of 10.9 g of the product obtained from the preceding Step A in 54.4 ml of ethylene glycol and 22 ml of ethyl orthoformate was heated to about 50° C. under an inert atmosphere.

220 mg of paratoluene sulfonic acid monohydrate were added and the mixture was stirred for about 3 hours, cooled to about 20° C. 4.2 ml of triethylamine and about 550 ml of water were poured into the mixture with stirring and the mixture was vacuum filtered. The product was washed with water and dried at 60° C. to obtain 12 g of (20, 20-ethylene dioxy pregn-5-ene 3α-yl) ethyl carbamate melting at ≈200° C.

Step C: 3α-methyl amino pregn-5-ene 20-one (N-methyl holamine) and its hydrochloride.

A suspension 1.145 g of aluminum and lithium hydride in 110 ml of tetrahydrofuran under an inert atmosphere was refluxed for 30 minutes and then a solution 6.51 g of the product of Step B in 65 ml of tetrahydrofuran was added thereto. The mixture was refluxed for 65 minutes. The temperature was reduced to 15° to 20° C. and 15 ml of water were cautiously added there to. Then, 15 ml of concentrated hydrochloric acid were added and stirred for 105 minutes and it was then made alkaline by the addition of 25 ml of potassium hydroxide and 5 ml of concentrated ammonia. The mixture was stirred for 10 minutes and 100 ml of a solution of Rochelle salt were added, and the decanted aqueous phase was extracted with ethyl acetate. The organic phase washed with saturated aqueous sodium chloride, dried and then evaporated to dryness under reduced pressure. The residue was recrystallized from ethyl acetate to obtain 4.07 g of 3α-methyl amino pregn-5-ene 20-one (N-methyl holamine) melting at 139° C.

Formation of the hydrochloride:

1.5 g of the base obtained from Step C were dissolved in 30 ml of ethyl acetate at 20° to 30° C. and an excess of hydrochloric acid dissolved in ethyl acetate was added thereto. The mixture was then chilled, vacuum filtered and the product washed with ethyl acetate, dried at 40° C. under reduced pressure and recrystallized from ethanol to obtain 1.31 g of the desired hydrochloride melting at 270° C.

Analysis: $C_{22}H_{36}NOCl$; molecular weight = 365.99

| | C % | H % | N % | Cl % |
|---|---|---|---|---|
| Calculated | 72.20 | 9.91 | 3.83 | 9.69 |
| Found | 72.4 | 10.1 | 3.8 | 9.7 |

EXAMPLE 2

(2-amino N-methyl N-(20-oxo-pregn-5-ene-3α-yl)acetamide and its fumarate.

Step A: 2-/(phenylmethoxy) carbonyl/amino/N-/20-oxopregn-5-ene-3α-yl/N-methyl acetamide 4.43 g of the free base obtained in Step C of Example 1 were dissolved in 130 ml of chloroform and 27 ml of triethylamine under an inert atmosphere and 5.6 g of N-(benzyloxy carbonyl) glycine (Z glycine) were added there to. Then in 20 minutes, with stirring, 3.89 g of 2-chloro N-methyl pyridinium iodide were added and after one hour 800 mg more iodide were added. The mixture was washed with an aqueous solution of 1 N hydrochloric acid then with an aqueous solution of 1 N sodium hydroxide and evaporated to dryness.

The mixture was purified by chromatography on silica gel and eluted with a mixture of 9 parts of methylene chloride and 1 part of ethyl acetate and was recrystallized from ethyl acetate to obtain 5.8 g of the product desired melting at 130° C., then 150° C.

Step B: 2-amino N-methyl N-(20-oxo pregn-5-ene 3α-yl) acetamide and its fumarate salt.

Hydrogen was bubbled through 6.2 g of the product of Step A is dissolved in 60 ml of tetrahydrofuran under an inert atmosphere and 1.2 g of 5% palladium on carbon catalyst and a after 2 hours the catalyst was filtered out and washed with methylene chloride and the filtrate was evaporated to dryness to obtain 4.55 g of a resinous material.

Formation of the fumarate 1.9 g of the said base were dissolved hot in 4 ml of ethanol 95° and 560 mg of fumaric acid dissolved hot in 6 ml of ethanol 95° were added thereto. Crystallization was induced and then the solution was chilled for about 1 hour. It was then vacuum filtered, washed with chilled ethanol, and dried at 60° C. under a vacuum. 2.02 g of the product desired was in the form of its hemihydrate melting at ≈160° C.

| Analysis: $C_{24}H_{38}N_2O_2 \cdot C_4H_4O_4 \cdot \tfrac{1}{2}H_2O$; molecular weight = 511.63 | | | | | | | | |
|---|---|---|---|---|---|---|---|---|
| Calculated | C % | 65.73 | H % | 8.67 | N % | 5.47 |
| Found | | 65.6 | | 8.5 | | 5.4 |

EXAMPLE 3

(2S) 2-amino N-(20-oxo pregn-5-ene 3α-yl) propionamide and its hydrochloride

Step A: 2-(1,1-dimethylethoxy) carbonyl amino N-(20-oxo pregn-5-ene 3α-yl) propionamide 3.15 g of the holamine of Example 1 and 2.08 g of tertbutyloxy carbonyl L-alanine (BOC L-alanine) were dissolved in 75 ml of chloroform and 15 ml of pyridine under an inert atmosphere and 2.1 g of 1-ethyl-3-(3-dimethyl amino propyl) carbodiimide hydrochloride was added thereto. The mixture was stirred for 1 hour and 15 minutes, washed with 2 N aqueous hydrochloric acid, then with an aqueous sodium bicarbonate solution, dried and evaporated to dryness under reduced pressure. The residue was chromatographed on silica gel and eluted with a 1:1 mixture of benzene:methyl ethyl ketone to obtain 4.5 g of 2-(1,1-dimethylethoxy) carbonyl amino N-(20-oxo pregn-5-ene 3α-yl) propionamide in the form of an oil.

Step B: (2S)-2-amino-N-(20-oxo pregn-5-ene 3α-yl)propionamide hydrochloride 4.5 g of the product of step A dissolved in 30 ml of 2 N hydrochloric acid in anhydrous methanol were stirred for about 2.5 hours under an inert atmosphere and the mixture was distilled to dryness under reduced pressure at 30° C. The residue was crystallized from ethyl acetate and the mixture vacuum filtered. The product was dissolved in 15 ml of methanol and the solution was filtered. 50 ml of ethyl acetate were added thereto and then the volume reduced to a half. The mixture was vacuum filtered and the product was dried at 40° C. under reduced pressure to obtain 2.5 g of (2S) 2-amino-N-(20-oxo pregn-5-ene 3α-yl)propionamide hydrochloride melting at 260° C.

| Analysis: $C_{24}H_{39}ClN_2O_2$; molecular weight = 423.03 | | | | | | | | |
|---|---|---|---|---|---|---|---|---|
| Calculated | C % | 68.14 | H % | 9.29 | N % | 6.62 | Cl % | 8.38 |
| Found | | 68.4 | | 9.3 | | 6.5 | | 8.5 |

EXAMPLE 4

2-amino N-(20 pregn-5-ene 3α-yl) acetamide hydrochloride

Using the method of example 2,N-(benzyloxycarbonyl) glycine was reacted with holamine to obtain 2-amino N-(20 oxo pregn-5-ene 3α-yl) acetamide hydrochloride which after crystallization from ethyl acetate melted at 205° C.

| Analysis: $C_{23}H_{36}N_2O_2$; molecular weight = 409.019 | | | | | | | | |
|---|---|---|---|---|---|---|---|---|
| Calculated | C % | 67.54 | H % | 9.12 | Cl % | 8.67 | N % | 6.85 |
| Found | | 67.8 | | 9.1 | | 8.5 | | 6.7 |

EXAMPLE 5

(2S) 2-amino N-(20-oxo pregn-5-ene 3α-yl) 1H-indole-3-propanamide fumarate

Using the procedure of example 3 BOC L-tryptophane and holamine were reacted to obtain (2S) 2-amino N-(20-oxo pregn-5-ene 3α-yl) 1H-indole-3-propanamide fumarate which after crystallization from methanol melted at 180° C.

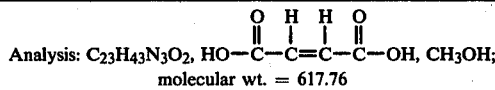

| Analysis: $C_{23}H_{43}N_3O_2$, $CH_3OH$; molecular wt. = 617.76 | | | | | | |
|---|---|---|---|---|---|---|
| Calculated | C % | 68.39 | H % | 7.91 | N % | 6.47 |
| Found | | 6.81 | | 8.0 | | 6.5 |

EXAMPLE 6

2-amino N-[(20S) 20-hydroxy pregn-5-ene 3α-yl)] acetamide hydrochloride

Step A: 3α-amino pregn-5-ene-20-ol

To a refluxing 100 ml of propanol were simultaneously added, over a period of 20 minutes, in small portions 5 g of sodium and a solution of 5 g of holamine in 5 ml of propanol while continuing reflux. After 1 hour and 25 minutes, the temperature was returned to ambient, the mixture chilled and acidified with acetic acid to $pH$ 6. The $pH$ raised to $pH$ 8 with potassium carbonate and the mixture was diluted with 500 ml of water, partially evaporated, 300 ml of water were added and the mixture was allowed to crystallize for 24 hours in the refrigerator. The filtered crystals were washed in water and dissolved in 10 ml of methylene chloride to which was added 50 ml of ethyl acetate and 30 ml of isopropyl ether. The methylene chloride was evaporated and the product allowed to crystallize during 16 hours in the refrigerator. 3 g of 3α-amino pregn-5-ene-20-ol was obtained melting at 160°.

Step 2: (20S) [3α-(trifluoroacetylamino) pregn-5-ene-20yl]trifluoroacetate 5.5 g of the product of Step A was dissolved in 55 ml of methylene chloride to which was added 5.5 ml of pyridine. The temperature was lowered to 0° C. and 5.5 ml of trifluoroacetic anhydride were added over 5 minutes. The mixture was stirred for 15 minutes at room temperature and brought to dryness. The residue was dissolved in cyclohexane and the solution filtered and concentrated to dryness. The residue was chromatographically separated on silica (eluant was cyclohexane: ethyl acetate 9:1) to obtain three fractions. The first was the (20R) isomer; the second (3.56 g) was a mixture of (20R) isomer and (20S) isomer; and the third (1.5 g) was the expected (20S) isomer which melted at 140° C.

Step C: (20S) 3α-amino pregn-5-ene-20-ol

A suspension of 2.4 g of the product of Step B in 24 ml of methanol was chilled in an ice bath and a aqueous solution of 2 N sodium hydroxide was added to it. The mixture was stirred for 2 hours and 30 minutes at ambient temperature and was diluted with water and extracted with methylene chloride. The organic phase was washed with a saturated solution of aqueous sodium chloride, and evaporated to dryness. 1.42 g of (20S) 3α-amino pregn-5-ene-20-ol melted at 190° C.

Step D: 2-amino-N-[(20S) 20-hydroxyl-pregn-5-ene-3α-yl]-acetamide hydrochloride

Using the procedure of example 2, Z-glycine was reacted with (20S) 3α-amino pregn-5-ene-20-ol to obtain 2-amino-N-[(20S) 20-hydroxy-pregn-5-ene-3α-yl]-acetamide hydrochloride after recrystallization from ethyl acetate, which melted at 264° C. (with decomposition)

Analysis: $C_{23}H_{38}N_2O_2 \cdot HCl$; molecular weight = 447.495

| | | C % | H % | | Cl % | | N % | |
|---|---|---|---|---|---|---|---|---|
| Calculated | | 67.20 | 9.56 | | 8.63 | | | 6.82 |
| Found | | 67.3 | 9.6 | | 8.7 | | | 6.8 |

EXAMPLE 7

A tablet was made containing 20 mg of 2-amino N-(20-oxo pregn-5-ene 3α-yl) acetamide hydrochloride and sufficient excipient for a final tablet weight of 100 mg. (The excipient was a mixture of lactose, starch, talc and magnesium stearate.)

Pharmacological Data

A. Adjuvant for anaphylactic shock

The administration to animals of a compound capable of stimulating the activity of immunitary systems leads to an increase in shock in response to administration of antigen to which the animal in sensitive. Male mice weighing between 30 to 35 g were sensitized by intraplantary administration of beef serum albumin. 8 days later, the mice received intraveinously an antigen and under the minimum sensitization conditions, the control animals were not in mortal shock at the time of the last administration.

The test compound was injected intraplantary admixed with an antigen and if the product was an adjuvant, it increased the sensitization and resulted in mortal shock with an intraveinous administration. The active dose which provoked a mortality equal to or greater than 50% of the animals was determined and the results are reported in Table I.

TABLE I

| Example No. | $LD_{50}$ Dose in mg |
|---|---|
| 4 | 1 |
| 6 | 4 |

B. Test of Rosettes to sheep red corpuscles

The administration to animals of a product capable of stimulating the immunitary systems leads to an increase of their capacity of reaction to the injection of a immunogenic product. 3 month old male rats were sensitized by intraperitoneal administration of sheep erythrocytoes on day 0 and 7 days later, the spleen was removed and splenocytes were placed in contact with sheep erythrocytes. The percentage of leucocytes around which the erythrocytes were in the form of rosettes was determined. The test compounds were orally administered daily from day-1 to day 1 and immunostimulating dose is the dose of product which multiplies by 2 the percentage of rosettes observed in the control animals. The results are reported in Table II.

TABLE II

| Example No. | Dose in mg/kg |
|---|---|
| 3 | 2 |
| 4 | 5 |

C. Acute toxicity

The acute toxicity was determined as the non lethal dose $LD_0$ by orally administering the test compounds to mice and the maximum dose which did not cause any mortality after 8 days was determined. The results are reported in Table III.

TABLE III

| Example No. | $LD_0$ in mg/kg |
|---|---|
| 3 | >400 |
| 4 | 600 |
| 6 | >400 |

Various modifications of the compounds and process of the invention may be made without departing from the spirit or scope thereof and it is to be understood that the invention is intended to be limited only as defined in the appended claims.

What we claim is:

1. A compound selected from the group consisting of 3-amino-Δ⁵-pregnenes of the formula I:

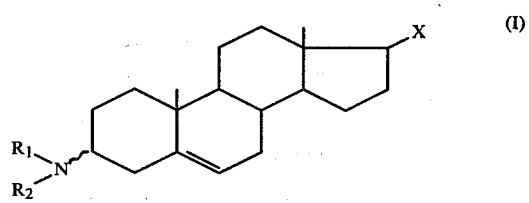

wherein X is selected from the group consisting of

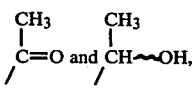

the wavy lines indicate that the group may be in the α- or β-position, $R_1$ is hydrogen, $R_2$ is selected from the group consisting of acyl of an α-amino-carboxylic acid or from a peptide of 2 to 3 amino acids of which amines may be either unsubstituted or mono- or disubstituted with alkyl of 1 to 5 carbon atoms with the proviso that if the 3-amino group is in the β-position, when X is

and $R_1$ is hydrogen, $R_2$ is not ethoxycarbonyl, the compound of the formula I wherein X is

$R_1$ is hydrogen and $R_2$ is methyl, the 3-amino group is in the α-position,
and their non-toxic, pharmaceutically acceptable acid addition salts.

2. A compound of claim 1 wherein the amino group is in the 3α position and their non-toxic pharmaceutically acceptable acid addition salts.

3. A compound of claim 2 wherein X is

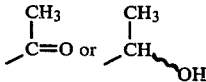

of which the hydroxy is in the 20α position.

4. A compound of claim 1 wherein the 3-amino-Δ⁵-pregnene is selected from the group consisting of 2-amino N-(20-oxo pregn-5-ene 3α-yl) acetamide and (2S) 2-amino-N-(20-oxo pregn-5-ene-3α-yl) propionamide and their non-toxic, pharmaceutically acceptable acid addition salts.

5. A compound of claim 1 which is 3α-methylamino-pregn-5-ene-20-one and its non-toxic, pharmaceutically acceptable acid addition salts.

6. A composition for the treatment of autoimmuno maladies comprising an autoimmuno stimulating effective amount of at least one compound of claim 1 in an inert pharmaceutical carrier.

7. A composition for the treatment of autoimmuno maladies comprising an autoimmuno stimulating effective amount of at least one compound of claim 2 in an inert pharmaceutical carrier.

8. A composition for the treatment of autoimmuno maladies comprising an autoimmuno stimulating effective amount of at least one compound of claim 3 in an inert pharmaceutical carrier.

9. A composition for the treatment of autoimmuno maladies comprising an autoimmuno stimulating effective amount of at least one compound of claim 4 in an inert pharmaceutical carrier.

10. A composition for the treatment of autoimmuno maladies comprising an autoimmuno stimulating effective amount of at least one compound of claim 5 in an inert pharmaceutical carrier.

11. A method of treating autoimmuno maladies in warm-blooded animals comprising administering to the warm-blooded animals an amount of at least one compound of claim 1 sufficient to treat autoimmuno maladies.

12. A method for treating autoimmuno maladies in warm-blooded animals comprising administering to a warm-blooded animal a therapeutically effective amount of at least one of the compounds set forth in claim 2.

13. A method for treating autiommuno maladies in warm-blooded animals comprising administering to a warm-blooded animal a therapeutically effective amount of at least one of the compounds set forth in claim 3.

14. A method for treating autoimmuno maladies in warm-blooded animals comprising administering to a warm-blooded animal a therapeutically effective amount of at least one of the compounds set forth in claim 4.

15. A method for treating autoimmuno maladies in warm-blooded animals comprising administering to a warm-blooded animal a therapeutically effective amount of at least one of the compounds set forth in claim 5.

16. A compound of claim 1 selected from the group consisting of 2-amino-N-methyl-N-(20-oxo-pregn-5-ene-3α-yl)-acetamide and its non-toxic, pharmaceutically acceptable acid addition salts.

17. A composition of claim 6 wherein the active compound is selected from the group consisting of 2-amino-N-methyl-N-(20-oxo-pregn-5-ene-3α-yl)-acetamide and its non-toxic, pharmaceutically acceptable acid addition salts.

18. The method of claim 11 wherein the active compound is selected from the group consisting of 2-amino-N-methyl-N-(20-oxo-pregn-5-ene-3α-yl)-acetamide and its non-toxic, pharmaceutically acceptable acid addition salts.

* * * * *